(12) United States Patent
Klieman et al.

(10) Patent No.: US 7,949,546 B1
(45) Date of Patent: May 24, 2011

(54) METHOD AND SYSTEM FOR PROVIDING FAMILY MEDICAL HISTORY DATA

(75) Inventors: Michael S. Klieman, Belmont, CA (US); Thomas Anthony Frasher, Sunnyvale, CA (US); Todd M. Fitch, Santa Clara, CA (US); Steven Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 359 days.

(21) Appl. No.: 11/925,022

(22) Filed: Oct. 26, 2007

(51) Int. Cl.
*G06F 15/16* (2006.01)

(52) U.S. Cl. .................. 705/3; 705/2; 600/300

(58) Field of Classification Search .......... 705/2–3; 600/300
See application file for complete search history.

(56) References Cited

U.S. PATENT DOCUMENTS

| | | | |
|---|---|---|---|
| 4,130,881 A * | 12/1978 | Haessler et al. | 705/3 |
| 5,692,501 A * | 12/1997 | Minturn | 600/301 |
| 5,772,585 A * | 6/1998 | Lavin et al. | 600/300 |
| 2003/0177030 A1* | 9/2003 | Turner et al. | 705/2 |
| 2008/0052113 A1* | 2/2008 | Cauley et al. | 705/2 |

* cited by examiner

*Primary Examiner* — Gerald J. O'Connor
*Assistant Examiner* — Sind Phongsvirajati
(74) *Attorney, Agent, or Firm* — Gunnison, McKay & Hodgson, L.L.P.; Philip McKay

(57) ABSTRACT

A method and system for providing family health history data includes a process for providing family health history data whereby, all, or part of, a family member's health data is obtained from, but not limited to, any of the following sources: the family member and/or agents of the family member; one or more other family members, one or more healthcare providers; one or more healthcare insurance plan providers; one or more healthcare benefit program administrators; one or more financial institutions; and/or any other source of a family member's health data. All, or part of, the family member's health data is then provided to other family members, healthcare providers for family members, state and/or private agencies, and/or any other party as designated by the family member, and on a selective access basis, as designated by the family member, for use as family health history data by the designated parties.

19 Claims, 2 Drawing Sheets

METHOD AND SYSTEM FOR PROVIDING FAMILY MEDICAL HISTORY DATA

BACKGROUND

An individual's health profile and healthcare history is often critical information that is required to provide the individual with competent medical advice, treatments, and care. As part of a complete health profile it is also often very important to have access to an individual's family health history in addition to the individual's own health profile and healthcare history. This is because many health conditions, and predispositions to health conditions, are genetic in nature and are therefore passed down from generation to generation. Consequently, an accurate family health history can help the individual and/or healthcare provider for the individual, take preventative actions, diagnose conditions and/or correlate symptoms with a given condition, recognize potential allergies and/or choose more effective treatments, and generally prescribe regimes, therapies, and/or procedures that are most likely to achieve positive results. In addition, an accurate family health history is valuable for determining lifestyle choices that may help the individual avoid, or mitigate a genetic predisposition to a condition and/or disease.

In addition, many third parties such as, but not limited to, schools, healthcare providers, private and government certification agencies, employers, and others, often request/require family health history information from an individual and request various forms be filled out providing this information.

In short, virtually any individual, and any healthcare providers for the individual, can benefit from access to the individual's family health history data/information. However, currently it is often very difficult for an individual or healthcare provider to gather, and maintain, accurate family healthcare history information. The situation has become even more problematic as people have become more mobile and family healthcare history information is scattered over multiple locations with multiple parties.

Currently, most family healthcare history data, if available at all, is obtained through family members via a healthcare version of the "oral tradition" whereby the information is passed down by word of mouth from generation to generation. This form of obtaining family healthcare history data is flawed, at best, and potentially dangerously inaccurate and/or incomplete. This is because as family members age their memories fail, family contacts are lost, and family members die. In addition, some individuals, such as adopted children and adoptive parents, do not have access to even this common, if flawed, source of family healthcare history data.

Herein, an individual's, and/or family member's, health data includes, but is not limited to: data representing any family member's health issues, particularly those known to have a genetic or multi-generational element or an environmental element; data representing all, or part of, a family member's past medical treatments; data indicating any recommended programs and/or medications for a family member; data representing all, or part of, the family member's family medical history, i.e., the family member's known family medical history; all, or part of, any clinical data regarding existing disease, diagnoses, and/or treatment programs associated with a family member; all, or part of, any data representing trends/patterns in a family member's clinical medical history and/or lab results; and/or any other data that is indicative of the family member's general health, health risks, health history, conditions, allergies, and/or pre-dispositions to disease and/or injury.

In addition, even if a given individual can locate all of his or her family members and gather some family health history information, in the present "information age", the average family member has significant amounts of health data/information generated each year. Consequently, over a period of several years, or a lifetime, the amount of family health history information can be overwhelming to both the individual and healthcare providers. This is particularly true if the family health history information is in printed or verbal form.

In many cases the family health history data must also be updated as family members age, conditions become known, and/or the family heath history information otherwise changes. This is often impossible, and even if possible, still usually means hours and hours of additional information gathering on the part of the individual and then hours and hours of data entry and/or organization by the individual, or another party. Consequently, currently, even if the some, or even all, family health history data is available, the individual often finds the process of obtaining the data too significant a burden and he or she simply abandons the project. In addition, even in instances where the individual puts in the required effort, family health history information obtained by an individual is again, all too often, reliant on memory, and/or comes from other somewhat dubious/unreliable sources.

Consequently, there is currently no relatively simple way for an individual to obtain, or share, family health history information and the problem of obtaining and maintaining accurate family health history information remains largely unsolved.

SUMMARY

In accordance with one embodiment, a method and system for providing family health history data includes a process for providing family health history data whereby, in one embodiment, all, or part of, one or more family member's health data is obtained from, but not limited to, any of the following sources: the family member and/or agents of the family member; one or more healthcare providers; one or more healthcare insurance plan providers; one or more healthcare benefit program administrators; one or more financial institutions; and/or any other source of a family member's health data. In one embodiment, all, or part of, the one or more family member's health data is obtained using and/or through a computing system implemented data management system. In one embodiment, all, or part of, the one or more family member's health data is then provided to one or more other family members, healthcare providers for one or more other family members, state and/or private agencies, and/or any other authorized user as designated by the family member, and on a selective access basis, as designated by the family member, for use as family health history data.

In one embodiment, all, or part of, the family member's health data is obtained from, but not limited to, any of the following sources: the family member; legal guardians for the family member; a private and/or government agency having jurisdiction over the family member and/or the family member's data; other family members; health insurance plan providers; health insurance plan administrators; healthcare expense account program providers; healthcare expense account program administrators; healthcare providers, such as doctors, nurses, hospitals, clinics, therapists, pharmacists, pharmacies, and/or technicians; employers; screen scraping data and/or websites containing the data, and/or any other sources and/or parties generating and/or having access to a family member's health data.

In one embodiment, all, or part of, the family member's health data is obtained using and/or through a computing system implemented data management system such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system.

In one embodiment, the family member's health data includes data representing information such as, but not limited to: the family member's historical utilization of the healthcare services; dates of healthcare service; types of healthcare service; medications prescribed; recommended programs and/or regimes; the family member's known family medical history; clinical data regarding existing or historical disease, diagnoses, allergies, surgeries, and/or treatment programs; data representing trends/patterns in the family member's specific clinical medical history and/or lab results; data indicating activities the family member takes part in; and/or any other data that is indicative of the family member's general health, health risks, health history, conditions, allergies, immunizations, and/or pre-dispositions to disease and/or injury and, in particular, genetic conditions.

In one embodiment, all, or part of, the family member's health data from one or more sources is aggregated, analyzed, and organized to create derived health data using a computing system implemented data management system.

In one embodiment, once the family member's raw and/or derived health data is obtained, all, or part, of the family member's health data is then provided to the process for providing family health history data based on the desires/conditions provided by the family member, legal guardians for the family member, and/or a private and/or government agency having jurisdiction over the family member and/or the family member's data.

In one embodiment, access and use of the family member's health data is then provided through the process for providing family health history data as prescribed by the family member, legal guardians for the family member, and/or a private and/or government agency having jurisdiction over the family member and/or the family member's data.

In one embodiment, access and use of the family member's health data is then provided through the process for providing family health history data to selected and/or designated parties including, but not limited to, other family members, and/or healthcare providers for other family members, as prescribed by the family member, legal guardians for the family member, and/or a private and/or government agency having jurisdiction over the family member and/or the family member's data.

In one embodiment, access and use of the family member's health data is then provided through the process for providing family health history data to selected and/or designated agencies and institutions including, but not limited to, adoption agencies and/or designated adoption services, adoptive parents and/or guardians, government agencies and/or healthcare providers, and/or any other institution and/or party as prescribed by the family member, legal guardians for the family member, and/or a private and/or government agency having jurisdiction over the family member and/or the family member's data.

In one embodiment, access and use of the family member's health data is then provided through the process for providing family health history data to selected and/or designated agencies and institutions including, but not limited to healthcare providers, and/or social and government agencies, and/or any other institution and/or party as prescribed by the family member, legal guardians for the family member, and/or a private and/or government agency having jurisdiction over the family member and/or the family member's data, for use in automatically filling in forms and/or otherwise providing required/requested family health history data to designated institutions and/or parties.

In one embodiment, access and use of the family member's health data is then provided through the process for providing family health history data to selected and/or designated agencies and institutions including, but not limited to research institutions and/or facilities, and/or a private and/or government agencies as prescribed by the family member, legal guardians for the family member, and/or a private and/or government agency having jurisdiction over the family member and/or the family member's data, for use in research and analysis of genetic disease and/or health conditions in general.

In one embodiment, a family member's raw and/or derived health data is updated, in one embodiment automatically, on either a periodic basis or as new data becomes available and then this updated data is made available to any of the parties discussed above through the process for providing family health history data disclosed herein.

Using the method and system for providing family health history data disclosed herein, all, or part of, a family member's health data is made available to designated parties, including other family members, without necessitating any significant additional effort on the part of the family member. The designated parties are then provided selective access to the data for use as family health history data. Consequently, using the method and system for providing family health history data disclosed herein, family members, and/or healthcare providers for family members, are provided potentially accurate and updated family health history data while a given family member still maintains complete control over the distribution and use of this potentially highly personal data. Therefore, using the method and system for providing family health history data disclosed herein, there is a greater chance that family heath history data will made available and/or shared in order to provide all family members with a more complete health profile and better healthcare opportunities.

As discussed in more detail below, using the below embodiments, with little or no modification and/or user input, there is considerable flexibility, adaptability, and opportunity for customization to meet the specific needs of various users under numerous circumstances.

Figure 1:
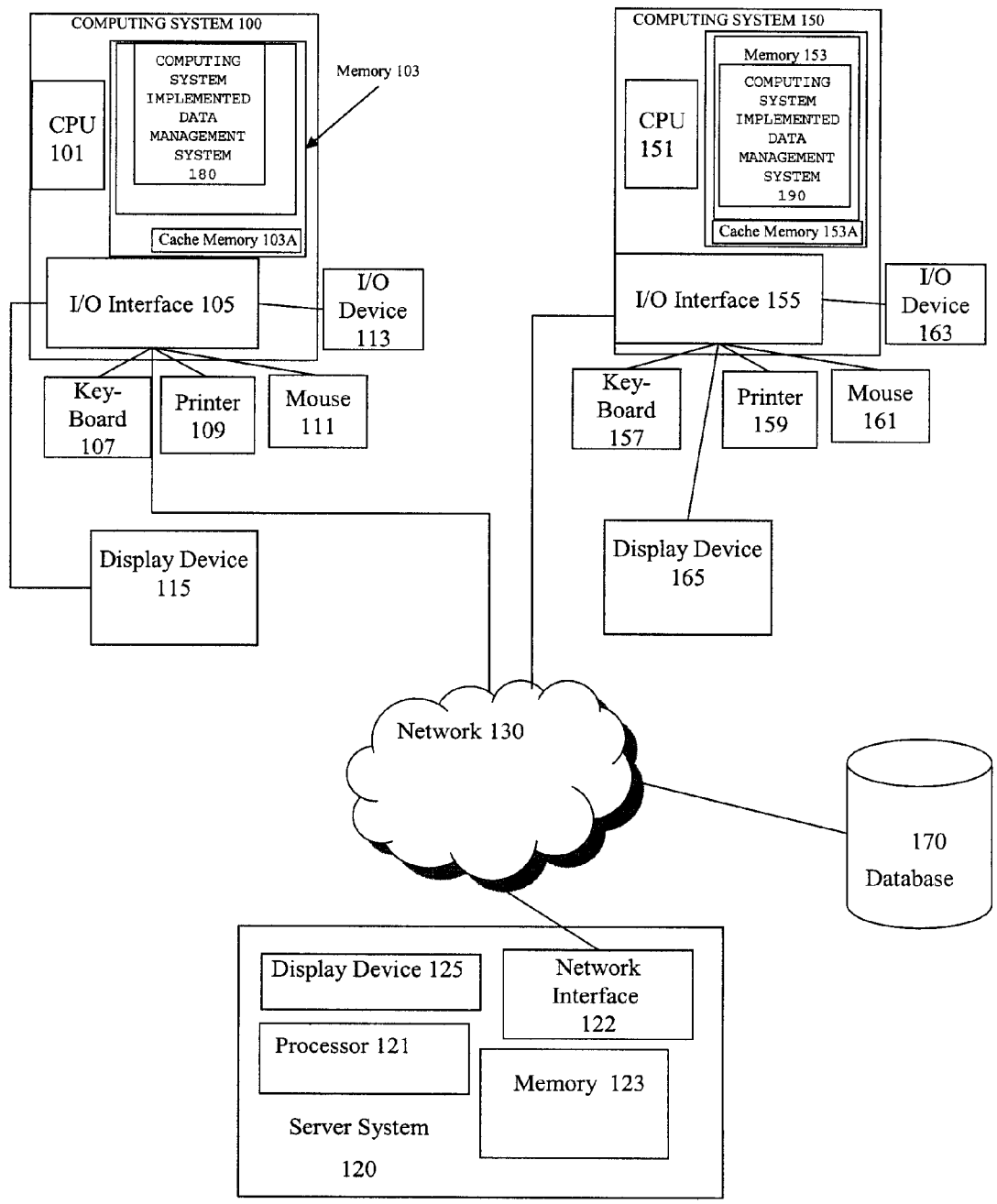
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian® OS, Windows® Mobile, or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, or other computing system capable of processing computer readable data, whether known at the time of filing or as developed later. Computing systems also include those in which one or more computing resources (hardware or software) are located remotely and accessed via network, such as a Local Area Network (LAN), Wide Area Network (WAN), a public network, such as the Internet, a private network, a combination of network types, a computing system bus, or other electronic medium in which data may be exchanged between one computing system and one or more other computing system(s), whether known at the time of filing or as developed later. Embodiments may be included as add-on software for existing software programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, delivered from a website and/or web-based function, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

Hardware System Architecture

FIG. 1 is a block diagram of an exemplary hardware architecture for implementing one embodiment of a system and method for providing family health history data, such as exemplary process 200 discussed herein, that includes: a computing system 100, e.g., a first computing system; a computing system 150, e.g., a second computing system; a server system 120; and a database 170, all operatively coupled by a network 130.

As seen in FIG. 1, computing system 100 typically includes a central processing unit (CPU) 101, an input/output (I/O) interface 105, and a memory system 103, including cache memory 103A. In one embodiment, memory system 103 includes all, or part of, a computing system implemented data management system 180 such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system. In one embodiment, computing system implemented data management system 180 is stored, in whole, or in part, in memory system 103, and is used by, or includes, as discussed below, a process for providing family health history data, such as exemplary process 200 discussed below.

Computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, computing system 100, whether available or known at the time of filing or as later developed. As discussed in more detail below, in one embodiment, a process for providing family health history data and/or a computing system implemented data management system are entered, in whole, or in part, into computing system 100 via I/O device 113, such as from a CD, DVD, floppy disk, portable hard drive, memory stick, download site, or other medium and/or computer program product as defined herein.

In one embodiment, computing system 100 is used, controlled, and/or accessible by a process for providing family health history data, and/or a computing system implemented data management system, and includes one or more family member's health data stored in or on memory 103, or cache memory 103A, or in another data storage device used, controlled, and/or accessible by computing system 100.

In one embodiment, computing system 100 is a computing system used and/or accessible by another computing system, such as computing system 150 (discussed below), a workstation, a two-way pager, a cellular telephone, a smart phone, a digital wireless telephone, a Personal Digital Assistant (PDA), a server computer, an Internet appliance, any other device, or any desired combination of these devices, that includes components that can execute all, or part, of a process for providing family health history data, and/or a computing system implemented data management system, in accordance with at least one of the embodiments as described herein.

Similarly, computing system 150 typically includes a CPU 151, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, whether available or known at the time of filing or as later developed.

In one embodiment, memory system 153 includes all, or part of, a computing system implemented data management system 190 such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system.

As discussed in more detail below, in one embodiment, all, or part of, a process for providing family health history data, and/or a computing system implemented data management system, can be loaded, in whole, or in part, into computing system 150 from computing system 100 for storage in memory system 153 and/or cache memory 153A.

In one embodiment, computing system 150 is used, controlled, and/or accessible by a process for providing family health history data, and/or a computing system implemented data management system, and includes one or more family member's health data stored in or on memory 153, or cache memory 153A, or in another data storage device used, controlled, and/or accessible by computing system 150.

In one embodiment, computing system 150 is a computing system used and/or accessible by another computing system, such as computing system 100 (discussed below), a workstation, a two-way pager, a cellular telephone, a smart phone, a digital wireless telephone, a Personal Digital Assistant (PDA), a server computer, an Internet appliance, any other device, or any desired combination of these devices, that includes components that can execute all, or part, of a process for providing family health history data, and/or a computing system implemented data management system, in accordance with at least one of the embodiments as described herein.

Also shown in FIG. 1 is exemplary database 170. In one embodiment, database 170 is a data storage device, a designated server system or computing system, or a designated portion of one or more server systems or computing systems, such as computing systems 100, 150 and 120, or a distributed database, or an external and/or portable hard drive. In one embodiment, database 170 is a dedicated mass storage device implemented in software, hardware, or a combination of hardware and software. In one embodiment, database 170 is a web-based function. As discussed in more detail below, in one embodiment, database 170 is under the control of the family member, and/or the family member's agents, and/or a process for providing family health history data, such as exemplary process 200, and/or a computing system implemented process, such as a computing system implemented data management system 180 and/or computing system implemented data management system 190.

In one embodiment, database 170 is used, controlled, and/or accessible by a process for providing family health history data, and/or a computing system implemented data management system, and includes one or more family member's health data. In one embodiment, database 170 is used, controlled, and/or accessible by a provider of and/or a system and process for providing family health history data, such as process for providing family health history data 200 and one or more family member's health data and/or health profile and medical history data is stored in database 170 in accounts associated with a given family member. In one embodiment, database 170 is used, controlled, and/or accessible by a provider of and/or a computing system implemented data management system, such as a computing system implemented data management system 180 and/or computing system implemented data management system 190.

In one embodiment, database 170 is used, controlled, and/or accessible by one or more healthcare insurance plan providers and/or healthcare benefit program administrators and includes one or more family members' health data.

In one embodiment, computing systems 100 and 150, and database 170, are coupled to a server system 120 through network 130. In one embodiment, server system 120 typically includes a server system display device 125, a server system processor 121, a server system memory 123, and a server system network interface 122.

In one embodiment, server system 120 is used in a station-to-station arrangement, such as a peer-to-peer, or hybrid peer-to peer, arrangement, as an indexing and/or central server used to connect a first computing system, such as computing system 100, and a second computing system, such as computing system 150. In one embodiment, some, or all, data and/or access rights are controlled locally and/or centrally. In some embodiments, some, or all, the publishing of data, and/or the receipt of data, is controlled in a peer-to-peer arrangement.

In one embodiment, server system 120 is used, controlled, and/or accessible by a process for providing family health history data, and/or a computing system implemented data management system, and includes one or more family member's health data. In one embodiment, server system 120 is used, controlled, and/or accessible by a provider of and/or a system and process for providing family health history data, such as process for providing family health history data 200 and one or more family members' health data and/or health profile and medical history data is stored in or by server system 120 in accounts associated with a given family member. In one embodiment, server system 120 is used, controlled, and/or accessible by a provider of and/or a computing system implemented data management system, such as a computing system implemented data management system 180 and/or computing system implemented data management system 190.

In one embodiment, server system 120 is used, controlled, and/or accessible by one or more healthcare insurance plan providers and/or healthcare benefit program administrators and includes one or more family members health data stored in or on memory 123, or in another data storage device used, controlled, and/or accessible by server system 120.

Network 130 can be any network or network system that is of interest to a user such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

Those of skill in the art will readily recognize that the components shown in FIG. 1, such as computing systems 100 and 150, database 170, server system 120, and their respective components, are shown for illustrative purposes only and that architectures with more or fewer components can implement, and benefit from, the invention. Moreover, one or more components of computing system 100, computing system 150, database 170, and server system 120 may be located remotely from their respective system and accessed via network, as discussed herein. In addition, the particular type of, and configuration of, computing systems 100 and 150, database 170, and server system 120 are not relevant.

As discussed in more detail below, in one embodiment, a process for providing family health history data, such as process for providing family health history data 200, and/or a computing system implemented data management system, such as a computing system implemented data management system 180 and/or computing system implemented data management system 190, are stored, in whole, or in part, in memory system 103 and/or cache memory 103A, of computing system 100, and/or memory system 153 and/or cache memory 153A of computing system 150, and/or in server memory system 123 of server system 120 and/or in database 170, and executed on computing system 100 and/or computing system 150. As used herein, a memory refers to a volatile memory, a non-volatile memory, or any combination of the two.

Although a process for providing family health history data, such as process for providing family health history data 200, and/or a computing system implemented data management system, such as computing system implemented data management system 180 and/or computing system implemented data management system 190, are sometimes referred to herein, alternatively, as a process, an application, a module, a program, a component of a software system, a component of a software package, a component of a parent system, a plug-in, or a feature of a parent system, this terminology is illustrative only. In some embodiments, a process for providing family health history data, such as process for providing family health history data 200, and/or a computing system implemented data management system, such as a computing system implemented data management system 180 and/or computing system implemented data management system 190, are capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPUs 101 and 151, or server system processor 121. In one embodiment, execution of a process by CPU 101, CPU 151, or server system processor 121, results in the operations of an agent computer process (not shown) and/or a rule computer process (not shown).

In one embodiment, a process for providing family health history data, such as process for providing family health history data 200, and/or a computing system implemented data management system, such as a computing system implemented data management system 180 and/or computing system implemented data management system 190, and/or a family member's health data, are computer applications or processes and/or data implemented and/or run and/or stored, in full, or in part, in, or on, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable data representing computer readable code, whether available or known at the time of filing or as later developed. This medium may belong to a computing system, such as computing systems 100 and 150 of FIG. 1, described above. However, in some embodiments, the medium also may be removable and/or remote from the computing system.

For example, all, or part, of a process for providing family health history data, such as process for providing family health history data 200, and/or a computing system implemented data management system, such as a computing system implemented data management system 180 and/or computing system implemented data management system 190, and/or a family member's health data, may be stored in a memory that is physically located in a location, such as server system memory 123, or database 170, of FIG. 1, different from a computing system, such as computing systems 100 and/or 150 of FIG. 1, utilizing a process for providing family health history data, and/or a computing system implemented data management system. In one embodiment, all, or part, of a process for providing family health history data, and/or a computing system implemented data management system, and/or a family member's health data, may be stored in a memory that is physically located, separate from the computing system's processor(s), such as CPUs 101 and 151 of FIG. 1, and the computing system CPUs can be coupled to the memory in a client-server system, such as server system 120 of FIG. 1, or, alternatively, via connection to another computer, such as computing systems 100, 150 of FIG. 1, via modems and analog lines, digital interfaces and a digital carrier line, or wireless or cellular connections.

In one embodiment, the computing systems and/or server systems, such as computing systems 100 and/or 150 and/or server system 120 of FIG. 1, running and/or utilizing and/or storing all, or part, of a process for providing family health history data, such as process for providing family health history data 200, and/or a computing system implemented data management system, such as a computing system implemented data management system 180 and/or computing system implemented data management system 190, and/or a family member's health data, is a portable computer, a workstation, a two-way pager, a cellular telephone, a smart phone, a digital wireless telephone, a PDA, a server computer, an Internet appliance, or any other device that includes components that can execute all, or part, of a process for providing family health history data, and/or a computing system implemented data management system, in accordance with at least one of the embodiments as described herein. Similarly, in another embodiment, a process for providing family health history data, and/or a computing system implemented data management system, and/or a family member's health data, may be implemented on and/or run and/or stored on a computing system and/or server system that is comprised of multiple different computers, wireless devices, cellular telephones, digital telephones, two-way pagers, personal digital assistants, server computers, or any desired combination of these devices, that are coupled to perform the processes and/or operations as described herein.

Process

Herein, the terms "family member", "user", and/or "patient" are used interchangeably to denote any party, including family members, interfacing and/or interacting with a process for providing family health history data, and/or a person who is the subject of all, or part of, any health data/information obtained by a process for providing family health history data, and/or a legal guardian of a person who is the subject of any health data/information obtained by a process for providing family health history data, and/or an authorized agent of any party interfacing and/or interacting with a process for providing family health history data, and/or a person who is the subject of any health data/information obtained by a process for providing family health history data, and/or any other authorized party associated with any party interfacing and/or interacting with a process for providing family health history data, and/or a person who is the subject of any health data/information obtained by a process for providing family health history data.

Herein, the terms "family" and/or "family member" are used interchangeably to denote one or more genealogical relatives of an individual, regardless of remoteness and/or degree of separation from the individual.

Herein, the term "healthcare" includes any general and/or specialized treatment, assessment, maintenance, therapy, medication, and/or advice relating to all, or any portion of, a family member's, state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; recommended activity level changes; other lifestyle changes; and/or surgical procedures; and/or any prescribed and/or suggested regime, medication, treatment, activity, avoided activity, and/or program designed to improve, maintain, and/or slow the degradation of, a family member's health.

Herein the terms "health data", "health information", "health data", "healthcare information", and/or "health profile and healthcare history information" are used interchangeably to denote, but is not limited to: data representing the historical utilization of healthcare services; data representing past medical treatments and/or claims; data indicating any recommended programs and/or medications; data representing known family medical history; clinical data regarding existing disease, diagnoses, allergies and/or treatment programs; data representing trends/patterns in specific clinical medical history and/or lab results; data indicating activities a family member takes/take part in; and/or any other data that is indicative of a family member's general health, health risks, health history, conditions, allergies, immunizations, and/or pre-dispositions to disease and/or injury.

Herein the term "derived health profile and healthcare history information" and "derived health data" denote health profile and healthcare history information and/or data derived based, at least in part, on information contained in a family member's health data such as, but not limited to: historical utilization of the healthcare services; current and historical health conditions; current and historical preventative medicine regime and/or usage; current and historical medication usage; history of surgical procedures; historical testing and exploratory procedure record and/or results; current and historical allergies and symptoms; immunization records; current and historical healthcare providers; current and historical medical and personal contacts; and any other health profile and medical history information capable of being derived from the family member's, health data, and of interest to the family member or another party.

Herein, the term "healthcare benefit program" and "health insurance plan" are used interchangeably to denote any policy, program, means and/or mechanism whereby a family member is provided benefits and/or service and/or entitlements to any form of healthcare.

Herein the terms "healthcare insurance plan providers" and "healthcare benefit program administrators" include, but are not limited to: health insurance plan providers; health insurance plan administrators; healthcare expense account program providers; healthcare expense account program administrators; healthcare providers; employers; and/or any other parties generating and/or having access to a family member's health data.

Herein, the term "healthcare provider" denotes any individuals, persons, agencies, institutions, organizations, businesses, and/or other entities that provide medical treatment, medications, therapy, advice, and/or equipment. For example, herein, the term "healthcare provider" includes, but is not limited to: doctors; nurses; technicians; therapists; pharmacists; counselors; alternative medicine practitioners; all medical facilities; doctor's offices; hospitals; emergency rooms; clinics; urgent care centers; alternative medicine clinics/facilities; physical therapy clinics/facilities; and any other party, entity, and/or facility providing general and/or specialized treatment, assessment, maintenance, therapy, medication, and/or advice relating to all, or any portion of, a family member's state of health, including but not limited to, general medical, specialized medical, surgical, dental, vision, psychological, and/or any other type of treatment, assessment, maintenance, therapy, medication, and/or advice.

In accordance with one embodiment, a method and system for providing family health history data includes a process for providing family health history data whereby, in one embodiment, all, or part of, one or more family member's health data is obtained from, but not limited to, any of the following sources: the family member and/or agents of the family member; one or more healthcare providers; one or more healthcare insurance plan providers; one or more healthcare benefit program administrators; one or more financial institutions; and/or any other source of a family member's health data. In one embodiment, all, or part of, the one or more family member's health data is obtained using and/or through a computing system implemented data management system. In one embodiment, all, or part of, the one or more family member's health data is then provided to one or more other family members, healthcare providers for one or more other family members, state and/or private agencies, and/or any other user as designated by the family member, and on a selective access basis, as designated by the family member, for use as family health history data by the designated users.

Figure 2:
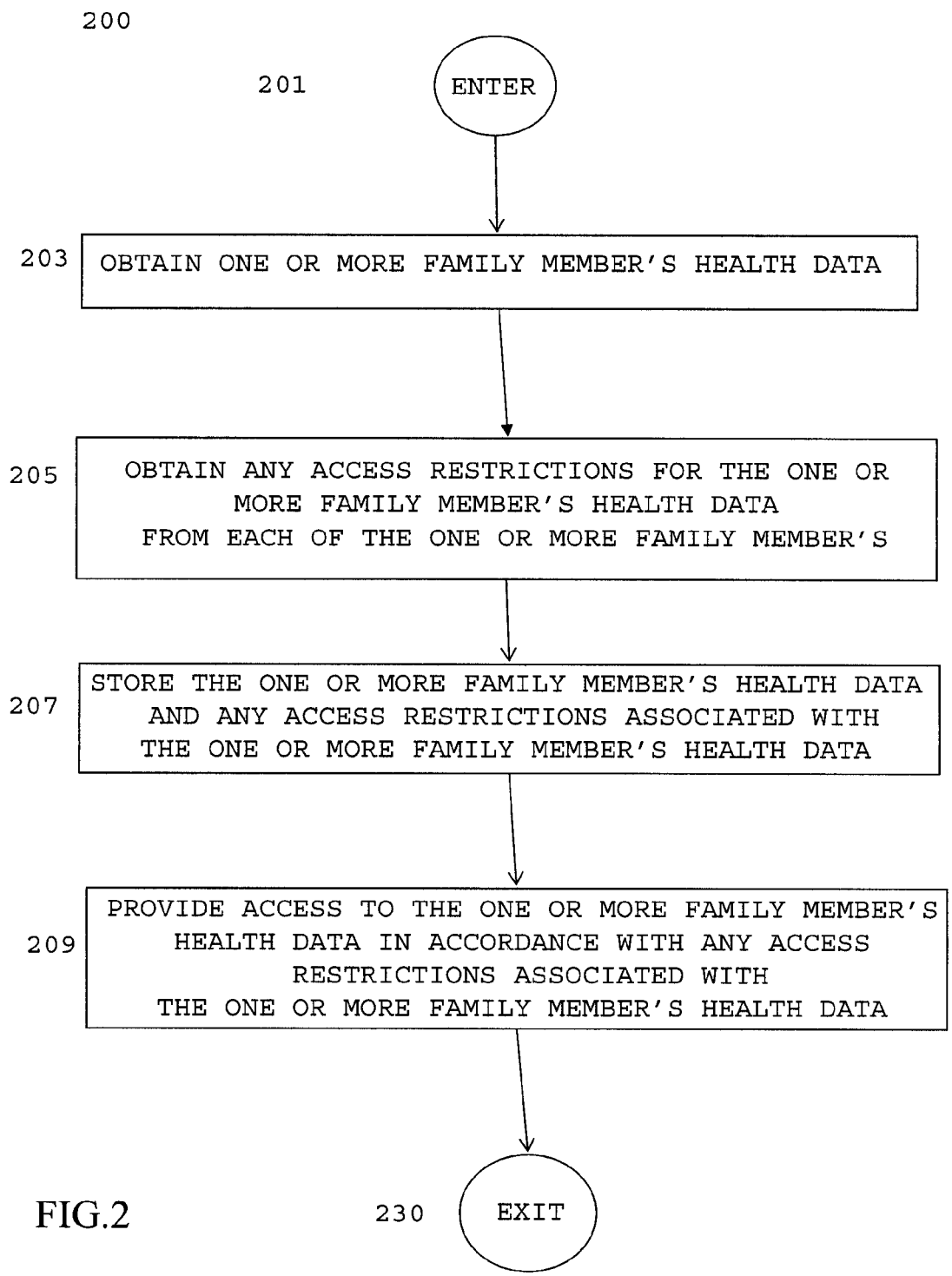
FIG. 2 is a flow chart depicting a process for providing family health history data in accordance with one embodiment.

FIG. 2 a flow chart depicting a process for providing family health history data 200 in accordance with one embodiment. Process for providing family health history data 200 begins at ENTER OPERATION 201 of FIG. 2 and process flow proceeds to OBTAIN ONE OR MORE FAMILY MEMBER'S HEALTH DATA OPERATION 203.

In one embodiment, at OBTAIN ONE OR MORE FAMILY MEMBER'S HEALTH DATA OPERATION 203 one or more family member's health data is obtained from one or more sources.

In one embodiment, the one or more family member's are contacted by one of the family members, or a healthcare provider for one or more of the family members, to request the related family member's health data.

In one embodiment, the one or more family member's are contacted by one of the family members, or a healthcare provider for one or more of the family members, to request the related family member's health data using a peer-to-peer arrangement or modified/hybrid peer-to peer arrangement. In one embodiment, a family member can also use the peer-to-peer arrangement or modified/hybrid peer-to peer arrangement to publish his or her health data for one or more other family members. In one embodiment, some, or all, data and/or access rights discussed below are controlled locally and/or centrally, while, as discussed above, some, or all, the publishing of data, and/or the receipt of data, is controlled in a peer-to-peer arrangement or modified/hybrid peer-to-peer arrangement.

In one embodiment, the existence of the at least one of the one or more family member's is provided by one of the other family members. In one embodiment, the existence of at least one of the one or more family member's is determined using genealogical data and/or a genealogical service or website.

In one embodiment, the existence of at least one of the one or more family member's is provided by one or more private and/or public and/or government agencies, such as an adoption agency, and the one or more family member's are contacted by and/or through the one or more private and/or public and/or government agencies to request the family member's health data.

In one embodiment, at OBTAIN ONE OR MORE FAMILY MEMBER'S HEALTH DATA OPERATION 203, all, or part of, the one or more family member's health data is obtained from, but not limited to, any of the following sources: the family member; legal guardians for the family member; a private and/or government agency having jurisdiction over the family member and/or the family member's data; other family members; health insurance plan providers; health insurance plan administrators; healthcare expense account program providers; healthcare expense account program administrators; healthcare providers, such as doctors, nurses, hospitals, clinics, therapists, pharmacists, pharmacies, and/or technicians; employers; screen scraping data and/or websites containing the data, and/or any other sources and/or parties generating and/or having access to a family member's health data.

In one embodiment, all, or part of, the one or more family member's health data is obtained using and/or through a computing system implemented data management system such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system. In one embodiment, the one or more family member's are connected through and/or by the computing system implemented data management system and/or by their common use of the computing system implemented data management system.

In one embodiment, the one or more family member's health data includes data representing information such as, but not limited to: a family member's historical utilization of healthcare services; dates of healthcare service; types of healthcare service; medications prescribed; recommended programs and/or regimes; a family member's known family medical history; clinical data regarding existing or historical disease, diagnoses, allergies, surgeries, and/or treatment programs; data representing trends/patterns in a family member's specific clinical medical history and/or lab results; and/or any other data that is indicative of a family member's general health, health risks, health history, conditions, allergies, immunizations, and/or pre-dispositions to disease and/or injury, and various other data that appears on a family member's healthcare claims and/or in a family member's healthcare record.

In one embodiment, the family member's health data is obtained by process for providing family health history data 200 from Explanation of Benefits (EOB) data provided to process for providing family health history data 200. According to one embodiment, copies of the EOBs, often in specific formats, are obtained by process for providing family health history data 200, and or a parent computing system implemented data management system, from one or more health insurance plan providers, health insurance plan administrators, healthcare expense account program providers, healthcare expense account program administrators, and/or healthcare providers. As discussed above, in one embodiment, process for providing family health history data 200 is part of a parent computing system implemented data management system, such as, but not limited to, personal healthcare management, personal financial, business financial, accounting, or tax preparation data management system, program, package or application, such as computing system implemented processes 180 and/or 190 of FIG. 1, that implements, includes, is accessed by, and/or is otherwise associated with process for providing family health history data 200. Some of these parent computing system implemented data management systems provide the capability to obtain, receive, and/or process electronic copies of the EOBs from one or more health insurance plan providers, health insurance plan administrators, healthcare expense account program providers, healthcare expense account program administrators, and/or healthcare providers, and then store the data for use by process for providing family health history data 200 in one of numerous locations by one of numerous methods known to those of skill in the art and/or as discussed herein.

In one embodiment, the family member's health data is obtained by process for providing family health history data 200 from invoices/patient bills and/or claims data provided to process for providing family health history data 200, and or a parent computing system implemented data management system, by one or more health insurance plan providers, health insurance plan administrators, healthcare expense account program providers, healthcare expense account program administrators, and/or healthcare providers.

As discussed above, in one embodiment, process for providing family health history data 200 is part of a parent computing system implemented data management system, such as, but not limited to, personal healthcare management, personal financial, business financial, accounting, or tax preparation data management system, program, package or application, such as computing system implemented processes 180 and/or 190 of FIG. 1, that implements, includes, is accessed by, and/or is otherwise associated with process for providing family health history data 200. Some of these parent systems provide the capability to obtain, receive, and/or process electronic copies of the invoices/claims from one or more health insurance plan providers, health insurance plan administrators, healthcare expense account program providers, healthcare expense account program administrators, and/or healthcare providers, often in their specific formats, and then store the data for use by process for providing family health history data 200 in one of numerous locations by one of numerous methods known to those of skill in the art and/or as discussed herein.

In one embodiment, the family member's health data is obtained by process for providing family health history data 200 from one or more of the following, either directly or by using screen scraping technology, or a similar technology: one or more healthcare insurance plan provider's, healthcare benefit program administrator's, and/or healthcare provider's, healthcare/patient management system/application; one or more healthcare insurance plan provider's, healthcare benefit program administrator's, and/or healthcare provider's, healthcare/patient management web-site; a financial and/or healthcare management system/application; a financial management and/or healthcare web-site; a general health information web-site; a general health insurance system/application; and/or a general health insurance web-site; and/or any other website, web-based function, application, screen display, or database.

In one embodiment, the family member's health data is obtained by process for providing family health history data 200 from any combination of the above sources and/or from any other source of a family member's health data whether known at the time of filing or as developed thereafter.

In addition, in some embodiments, a family member's health data is obtained from multiple sources of the same type. For instance, in one embodiment, a family member's health data comes from: two or more health insurance plan providers; and/or two or more health insurance plan administrators; and/or two or more healthcare expense account program providers; and/or two or more healthcare expense account program administrators; and/or two or more healthcare providers; and/or two or more family members. In one embodiment, this gives process for providing family health history data 200 the ability to provide the family member with a more complete and accurate health profile and medical history.

In one embodiment, at OBTAIN ONE OR MORE FAMILY MEMBER'S HEALTH DATA OPERATION 203, all, or part of, the one or more family member's health data is obtained directly from the family member and/or the family members data sources discussed above. In some embodiments, at OBTAIN ONE OR MORE FAMILY MEMBER'S HEALTH DATA OPERATION 203, all, or part of, the one or more family member's health data is obtained from other family members, or any other person, party or source, having information regarding the family member.

In one embodiment, at OBTAIN ONE OR MORE FAMILY MEMBER'S HEALTH DATA OPERATION 203, all, or part of, the one or more family member's health data obtained is weighted by a relationship weighting factor and/or scale based on, among other things, the relationship of the family member to a given family member in question. For instance, health data associated with a family member representing a direct parental link might, in a specific instance, be given a larger weighting factor than health data associated with a cousin.

In one embodiment, at OBTAIN ONE OR MORE FAMILY MEMBER'S HEALTH DATA OPERATION 203, all, or part of, the one or more family member's health data obtained is weighted by a source weighting factor and/or scale based on, among other things, the source of the health data regarding the family member. For instance, health data associated with a family member coming from that family member, or that family member's records and/or data, might be given a larger weighting factor than health data associated with a family member coming from another family member or third party.

As noted above, in one embodiment, at OBTAIN ONE OR MORE FAMILY MEMBER'S HEALTH DATA OPERATION 203, all, or part of, the one or more family member's health data is obtained from the biological parents of an adopted child. In one embodiment, in this instance, to preserve the anonymity of the biological parents, at OBTAIN ONE OR MORE FAMILY MEMBER'S HEALTH DATA OPERATION 203, the existence of at least one of the one or more family member's is provided by one or more private and/or public and/or government agencies, such as an adoption agency, and the one or more family member's are contacted by and/or through the one or more private and/or public and/or government agencies to request the one or more family member's health data. The one or more family member's health data is then provided to the one or more private and/or public and/or government agencies which, in turn, make the data available to process for providing family health history data 200 in such a way as to not divulge the identity of the one or more family members and/or the location of the adopted child.

In one embodiment, at OBTAIN ONE OR MORE FAMILY MEMBER'S HEALTH DATA OPERATION 203, all, or part of, the one or more family member's health data is obtained by process for providing family health history data 200 from any of the sources discussed above, via any means for obtaining, collecting, accessing, entering, transferring, relaying and/or providing data in any form, to a process, such as process for providing family health history data 200, whether known at the time of filing or as developed thereafter.

For instance, in one embodiment, at OBTAIN ONE OR MORE FAMILY MEMBER'S HEALTH DATA OPERATION 203, all, or part of, the one or more family member's health data is obtained by process for providing family health history data 200 from any of the sources discussed above through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, at OBTAIN ONE OR MORE FAMILY MEMBER'S HEALTH DATA OPERATION 203, all, or part of, the one or more family member's health data is obtained by process for providing family health history data 200 from any of the sources discussed above through e-mail or through text messaging. In other embodiments, at OBTAIN ONE OR MORE FAMILY MEMBER'S HEALTH DATA OPERATION 203, all, or part of, the one or more family member's health data is obtained by process for providing family health history data 200 from any of the sources discussed above using any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once one or more family member's health data is obtained from one or more sources at OBTAIN ONE OR MORE FAMILY MEMBER'S HEALTH DATA OPERATION 203, process flow proceeds to OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 is provided the opportunity to define and/or implement access restrictions to be applied to all, or any designated part, of their respective health data obtained at OBTAIN ONE OR MORE FAMILY MEMBER'S HEALTH DATA OPERATION 203.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only selected and/or designated parties including, but not limited to, other family members, are given access to all, or any designated part, of the family member's health data.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only healthcare providers for other family members are given access to all, or any designated part, of the family member's health data.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only specified and/or designated agencies and institutions including, but not limited to, adoption agencies and/or designated adoption services, adoptive parents and/or guardians, government agencies and/or healthcare providers, and/or any other specified institution and/or party are given access to all, or any designated part, of the family member's health data, and, in one embodiment, only for specified purposes.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only selected and/or designated agencies and institutions including, but not limited to, schools, healthcare providers, employers, insurance providers, and/or a private and/or government agencies are given access to all, or any designated part, of the family member's health data, and, in one embodiment, only for specified purposes such as for use in automatically filling in forms and/or otherwise providing required/requested family health history data, and, in one embodiment, only for specified purposes/questions.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only selected and/or designated agencies and institutions including, but not limited to, research institutions and/or facilities, and/or a private and/or government agencies are given access to all, or any designated part, of the family member's health data, and, in one embodiment, only for specified purposes such as for use in research and analysis of genetic disease and/or health conditions in general.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that all, or any designated part, of the family member's health data can only be used under the condition of maintain the anonymity of the family member.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only specifically designated portions of the family member's health data can be accessed by any, or all, parties given access to the family member's health data.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that only specific classes of the family member's health data, such as physical as opposed to mental health data, can be accessed by any, or all, parties given access to the family member's health data.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that access is granted only in response to specific symptoms and/or queries made by another family member and/or healthcare provider and/or designated party.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that access is granted the family member's health data only on a case-by-case basis, with each request for data needing the family members specific approval.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements access restrictions to be applied to all, or any designated part, of their respective health data obtained at OBTAIN ONE OR MORE FAMILY MEMBER'S HEALTH DATA OPERATION 203 such that access is granted the family member's health data only after specific events, such as the death of the family member.

In one embodiment, at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, each of the family members, legal guardians for the family member, and/or a private and/or government agency having jurisdiction over the family member and/or the family member's data of OBTAIN ONE OR MORE FAMILY MEMBER'S HEALTH DATA OPERATION 203 defines and/or implements any access restrictions to be applied to all, or any designated part, of their respective health data obtained at OBTAIN ONE OR MORE FAMILY MEMBER'S HEALTH DATA OPERATION 203 that the family member, legal guardian for the family member, and/or a private and/or government agency having jurisdiction over the family member and/or the family member's data desires.

In one embodiment, once each of the family members, legal guardians for the family member, and/or a private and/or government agency having jurisdiction over the family member and/or the family member's data of OBTAIN ONE OR MORE FAMILY MEMBER'S HEALTH DATA OPERATION 203 is provided the opportunity to define and/or implement access restrictions to be applied to all, or any designated part, of their respective health data obtained at OBTAIN ONE OR MORE FAMILY MEMBER'S HEALTH DATA OPERATION 203 at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, process flow proceeds to STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207.

In one embodiment, at STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207 the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205 are stored, in whole, or in part, in one or more databases maintained by, accessible by, owned by, or otherwise related to, a provider of, and/or, process for providing family health history data 200, any one or more of the one or more family members of OBTAIN ONE OR MORE FAMILY MEMBER'S HEALTH DATA OPERATION 203, a provider of, and/or, a computing system implemented data management system, by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing system, such as computing system 100 described above. In one embodiment, the data, in whole, or in part, is stored in any computing system and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205 stored as described above is maintained, in whole, or in part, by: a provider of, and/or, process for providing family health history data 200; any one or more of the one or more family members of OBTAIN ONE OR MORE FAMILY MEMBER'S HEALTH DATA OPERATION 203; a provider of, and/or, a computing system implemented data management system; a third party data storage institution; any third party service or institution; or any other parties. In some of these embodiments, access to the data is then granted to process for providing family health history data 200 by providing access to the data and/or providing the data on a computer program product.

In some embodiments, the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, stored as described above, are updated as needed and/or periodically. In one embodiment, the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, stored as described above, are updated automatically by obtaining new data from any of the sources discussed above on a periodic basis. In one embodiment, the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, stored as described above, are updated semi-automatically in response to an action and/or request by the family member or another authorized party, either as needed or on a periodic basis. In one embodiment, the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205, stored as described above, are updated manually by the family member or another authorized party, either as needed or on a periodic basis.

In one embodiment, once the one or more family member's health data of OBTAIN ONE OR MORE FAMILY MEMBER'S HEALTH DATA OPERATION 203 and any access restrictions of OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205 is stored, in whole, or in part, at STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207, process flow proceeds to PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 the family member's heath data is provided to one or more of the designated parties of STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207 in accordance with any access restrictions of STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207.

For instance, in one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209, only selected and/or designated parties including, but not limited to, other family members, are given access to all, or any designated part, of the family member's health data.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only healthcare providers for other family members are given access to all, or any designated part, of the family member's health data.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only specified and/or designated agencies and institutions including, but not limited to, adoption agencies and/or designated adoption services, adoptive parents and/or guardians, government agencies and/or healthcare providers, and/or any other specified institution and/or party are given access to all, or any designated part, of the family member's health data, and, in one embodiment, only for specified purposes.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only selected and/or designated agencies and institutions including, but not limited to healthcare providers, schools, and/or social and government agencies, and/or any other institution and/or party are given access to all, or any designated part, of the family member's health data, and, in one embodiment, only for specified purposes such as for use in automatically filling in forms and/or otherwise providing required/requested family health history data, and, in one embodiment, only for specified purposes/questions.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only selected and/or designated agencies and institutions including, but not limited to research institutions and/or facilities, and/or a private and/or government agencies are given access to all, or any designated part, of the family member's health data, and, in one embodiment, only for specified purposes such as for use in research and analysis of genetic disease and/or health conditions in general.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 all, or any designated part, of the family member's health data can only be used under the condition of anonymity.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only specifically designated portions of the family member's health data can be accessed by any, or all, parties given access to the family member's health data.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 only specific classes of the family member's health data, such as physical as opposed to mental health data, can be accessed by any, or all, parties given access to the family member's health data.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 access is granted only in response to specific symptoms and/or queries made by another family member and/or healthcare provider and/or designated party.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 access is granted the family member's health data only on a case-by-case basis, with each request for data needing the family members specific approval.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 access is granted to all, or a designated part of, the family member's health data only after specific events, such as the death of the family member.

In one embodiment, at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209 access is granted the family member's health data only in accordance with any conditions desired/specified by that the family member, legal guardian for the family member, and/or a private and/or government agency having jurisdiction over the family member and/or the family member's data and set forth at OBTAIN ANY ACCESS RESTRICTIONS FOR THE ONE OR MORE FAMILY MEMBER'S HEALTH DATA FROM EACH OF THE ONE OR MORE FAMILY MEMBER'S OPERATION 205.

In one embodiment, once the family member's heath data is provided to one or more of the designated parties of STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207 in accordance with any access restrictions of STORE THE ONE OR MORE FAMILY MEMBER'S HEALTH DATA AND ANY ACCESS RESTRICTIONS ASSOCIATED WITH THE ONE OR MORE FAMILY MEMBER'S HEALTH DATA OPERATION 207 at PROVIDE ACCESS TO THE ONE OR MORE FAMILY MEMBER'S HEALTH DATA IN ACCORDANCE WITH ANY ACCESS RESTRICTIONS ASSOCIATED WITH THE ONE OR MORE FAMILY MEMBER'S HEALTH DATA OPERATION 209, process flow proceeds to EXIT OPERATION 230.

In one embodiment, at EXIT OPERATION 230 process for providing family health history data 200 is exited to await new data and/or updates.

Using process for providing family health history data 200, all, or part of, a family member's health data is made available to designated parties, including other family members, without necessitating any significant additional effort on the part of the family member. The designated parties are then provided selective access to the data for use as family health history data. Consequently, using process for providing family health history data 200, individuals, and/or healthcare providers for individuals, are provided potentially accurate and updated family health history data while the family member still maintains complete control over the distribution and use of this potentially highly personal data. Therefore, using process for providing family health history data 200, there is a greater chance that family heath history data will be made available and/or shared in order to provide all family members with a more complete health profile and better healthcare opportunities.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "defining", "accessing", "analyzing", "obtaining", "deriving", "determining", "collecting", "creating", "transferring", "storing", "comparing", "storing", "providing", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A system for providing family health history data comprising:
   a processor for executing at least part of a process for providing family health history data, the process for providing family health history data comprising:
   aggregating health data associated with two or more family members of a given family from a plurality of different sources at different remote locations, at least a portion of the health data being obtained by the process for providing family health history electronically from a remote website of one of either a healthcare provider or a health insurance provider, at least a portion of the health data being obtained from individual ones of the family members, a guardian of one or more of the family members if such a guardian is assigned, a private and/or government agency having jurisdiction over one or more of the family members if such a jurisdiction exists over a family member, wherein different portions of the obtained data are weighted by relationship weighting factors based on the relationship of any given family member with any other given family member, the relationship weighting factors being greater for closer genetic links;
   providing each of the two or more family members, or their authorized agents if such authorized agents exist, the capability to place restrictions on the access to at least part of the health data associated with the respective family members; and
   providing or denying a party access to portions of the health data associated with the family in accordance with the access restrictions placed on the portions of the health data by individual ones of the family members associated with each portion.

2. The system for providing family health history data of claim 1, wherein;
   the restrictions on the access to at least part of the health data associated with the family member comprise at least one accessing party restriction designating what parties may access at least part of the health data associated with the family member.

3. The system for providing family health history data of claim 2, wherein;
   at least one accessing party restriction comprises one of the following accessing party restrictions:
   the accessing party must be a designated family member;
   the accessing party must be a healthcare provider; or
   the accessing party must be an authorized party.

4. The system for providing family health history data of claim 1, wherein;
   the restrictions on the access to at least part of the health data associated with the family member comprise at least one content accessing restriction designating what portion of the health data associated with the family member may be accessed.

5. The system for providing family health history data of claim 4, wherein;
   at least one content accessing restriction designating what portion of the health data associated with the family member may be accessed comprises one of the following content accessing restrictions:
   the accessing party is given access to only a designated portion of the health data associated with the family member;

the accessing party is given access to only designated classes of the health data associated with the family member;

the accessing party is given access to only the health data associated with the family member associated with health issues having a genetic link; or the accessing party is given access to only the health data associated with the family member that is related to a specific symptom.

6. The system for providing family health history data of claim 1, wherein;

the family member is a biological family member of an adopted child; and the party given access to the at least part of the health data associated with the biological family member of the adopted child is a party and or agency obtaining the data on behalf of the adopted child.

7. The system for providing family health history data of claim 1, wherein;

the party provided access to the at least part of the health data associated with the family member is provided the access to the at least part of the health data associated with the family member for filling in a form requesting family health history data.

8. A system for providing family health history data comprising:

one or more computing system implemented data management systems; and a processor for executing at least part of a process for providing family health history data, the process for providing family health history data comprising:

aggregating health data associated with two or more family members of a given family from a plurality of different sources at different remote locations, at least a portion of the health data being obtained by the process for providing family health history electronically from a remote website of one of either a healthcare provider or a health insurance provider, at least a portion of the health data being obtained from individual ones of the family members, a guardian of one or more of the family members if such a guardian is assigned, a private and/or government agency having jurisdiction over one or more of the family members if such a jurisdiction exists over a family member, wherein different portions of the obtained data are weighted by relationship weighting factors based on the relationship of any given family member with any other given family member, the relationship weighting factors being greater for closer genetic links;

providing each of the two or more family members, or their authorized agents if such authorized agents exist, the capability to place restrictions on the access to at least part of the health data associated with the respective family members; and providing or denying a party access to portions of the health data associated with the family in accordance with the access restrictions placed on the portions of the health data by individual ones of the family members associated with each portion.

9. The system for providing family health history data of claim 8, wherein;

the one or more computing system implemented data management systems comprise at least one a computing system implemented healthcare management system.

10. The system for providing family health history data of claim 8, wherein;

the one or more computing system implemented data management systems comprise at least one computing system implemented personal financial management system.

11. The system for providing family health history data of claim 8, wherein;

the restrictions on the access to at least part of the health data associated with the family member comprise at least one accessing party restriction designating what parties may access at least part of the health data associated with the family member.

12. The system for providing family health history data of claim 8, wherein;

the restrictions on the access to at least part of the health data associated with the family member comprise at least one content accessing restriction designating what portion of the health data associated with the family member may be accessed.

13. A computer program product for providing family health history data comprising:

a tangible computer readable medium;

and computer program code, encoded on the computer readable medium, comprising computer readable instructions for:

aggregating health data associated with two or more family members of a given family from a plurality of different sources at different remote locations, at least a portion of the health data being obtained by the process for providing family health history electronically from a remote website of one of either a healthcare provider or a health insurance provider, at least a portion of the health data being obtained from individual ones of the family members, a guardian of one or more of the family members if such a guardian is assigned, a private and/or government agency having jurisdiction over one or more of the family members if such a jurisdiction exists over a family member, wherein different portions of the obtained data are weighted by relationship weighting factors based on the relationship of any given family member with any other given family member, the relationship weighting factors being greater for closer genetic links;

providing each of the two or more family members, or their authorized agents if such authorized agents exist, the capability to place restrictions on the access to at least part of the health data associated with the respective family members; and providing or denying a party access to portions of the health data associated with the family in accordance with the access restrictions placed on the portions of the health data by individual ones of the family members associated with each portion.

14. The computer program product for providing family health history data of claim 13, wherein;

the restrictions on the access to at least part of the health data associated with the family member comprise at least one accessing party restriction designating what parties may access at least part of the health data associated with the family member.

15. The computer program product for providing family health history data of claim 14, wherein;

at least one accessing party restriction comprises one of the following accessing party restrictions:

the accessing party must be a designated family member;

the accessing party must be a healthcare provider; or the accessing party must be an authorized party.

16. The computer program product for providing family health history data of claim 13, wherein;

the restrictions on the access to at least part of the health data associated with the family member comprise at least one content accessing restriction designating what portion of the health data associated with the family member may be accessed.

17. The computer program product for providing family health history data of claim 16, wherein;
at least one content accessing restriction designating what portion of the health data associated with the family member may be accessed comprises one of the following content accessing restrictions:
the accessing party is given access to only a designated portion of the health data associated with the family member;
the accessing party is given access to only designated classes of the health data associated with the family member;
the accessing party is given access to only the health data associated with the family member associated with health issues having a genetic link; or
the accessing party is given access to only the health data associated with the family member that is related to a specific symptom.

18. The computer program product for providing family health history data of claim 13, wherein;
the family member is a biological family member of an adopted child; and
the party given access to the at least part of the health data associated with the biological family member of the adopted child is a party and/or agency obtaining the data on behalf of the adopted child.

19. The computer program product for providing family health history data of claim 13, wherein;
the party provided access to the at least part of the health data associated with the family member is provided the access to the at least part of the health data associated with the family member for filling in a form requesting family health history data.

\* \* \* \* \*

UNITED STATES PATENT AND TRADEMARK OFFICE
CERTIFICATE OF CORRECTION

| | | |
|---|---|---|
| PATENT NO. | : 7,949,546 B1 | Page 1 of 1 |
| APPLICATION NO. | : 11/925022 | |
| DATED | : May 24, 2011 | |
| INVENTOR(S) | : Michael S. Klieman et al. | |

It is certified that error appears in the above-identified patent and that said Letters Patent is hereby corrected as shown below:

In Column 27, Line 62, Claim 9, between "at least one" and "computing" delete "a".

Signed and Sealed this
Second Day of October, 2012

David J. Kappos
*Director of the United States Patent and Trademark Office*